US012670231B2

(12) United States Patent
Wang et al.

(10) Patent No.: US 12,670,231 B2
(45) Date of Patent: Jun. 30, 2026

(54) MACHINE LEARNING FOR NON-IMAGING DATA USING TASK-DEPENDENT FEATURE DEPENDENCIES

(71) Applicant: INTERNATIONAL BUSINESS MACHINES CORPORATION, Armonk, NY (US)

(72) Inventors: Hongzhi Wang, Santa Bruno, CA (US); Andrea Giovannini, Zurich (CH); Kristen Beck, San Jose, CA (US); Tanveer Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 877 days.

(21) Appl. No.: 17/988,745

(22) Filed: Nov. 16, 2022

(65) Prior Publication Data

US 2024/0169028 A1 May 23, 2024

(51) Int. Cl.
| | |
|---|---|
| *G06F 18/213* | (2023.01) |
| *G06F 18/2431* | (2023.01) |
| *G06F 18/25* | (2023.01) |
| *G06N 3/096* | (2023.01) |
| *G06V 10/80* | (2022.01) |
| *G06V 10/82* | (2022.01) |
| *G16H 30/40* | (2018.01) |

(52) U.S. Cl.
CPC ........ *G06F 18/213* (2023.01); *G06F 18/2431* (2023.01); *G06F 18/25* (2023.01); *G06V 10/80* (2022.01); *G06V 10/82* (2022.01);

*G06N 3/096* (2023.01); *G06T 2207/20084* (2013.01); *G16H 30/40* (2018.01)

(58) Field of Classification Search
CPC ........ G06F 18/213; G06V 10/82; G06N 3/08; G06N 3/096; G06T 2207/20084; G16H 30/40; G16H 50/30
See application file for complete search history.

(56) References Cited

U.S. PATENT DOCUMENTS

| | | | |
|---|---|---|---|
| 6,789,069 | B1 | 9/2004 | Barnhill et al. |
| 2005/0143928 | A1 | 6/2005 | Moser et al. |
| 2014/0012866 | A1 | 1/2014 | Bowman et al. |
| 2019/0336108 | A1* | 11/2019 | Hope Simpson ..... G06T 7/0012 |

OTHER PUBLICATIONS

Panayides et al., NPL ("AI in Medical Imaging Informatics: Current challenges and Future Directions" Published Jul. 2000 by IEEE Total 21 pages (Year: 2000).*

(Continued)

*Primary Examiner* — Quoc A Tran
(74) *Attorney, Agent, or Firm* — CHIP LAW GROUP

(57) ABSTRACT

Machine learning using dependency priors includes determining task-dependent feature dependencies for a group of features extracted from non-imaging data received with the computer hardware. The non-imaging data can be reformatted based on the task-dependent feature dependencies. The reformatting can convert strongly dependent features among the group of features into one or more subgroups based on task-specific, feature dependency-based priors. Based on the reformatted data, a machine learning prediction can be generated by a machine learning model.

20 Claims, 5 Drawing Sheets

(56)                    References Cited

OTHER PUBLICATIONS

Sharma, A. et al., "DeepInsight: A methodology to transform a non-image data to an image for convolution neural network architecture." Sci Rep 9, 11399 (2019), 7 pg.

Sharma, A. et al., "DeepInsight-FS: Selecting features for non-image data using convolutional neural network" bioRxiv, Sep. 19, 2020, retrieved from the Internet: <https://www.biorxiv.org/content/10.1101/2020.09.17.301515v1>, 13 pg.

Kovalerchuk, B. et al., "Solving Non-Image Learning Problems by Mapping to Images," 2020 24th International Conference Information Visualisation (IV), 2020, pp. 264-269.

Ma, S. et al., "OmicsMapNet: Transforming omics data to take advantage of Deep Convolutional Neural Network for discovery," Submitted on Apr. 14, 2018 (v1), last revised May 23, 2019 (this version, v2), retrieved from the Internet: <https://arxiv.org/abs/1804.05283>, 33 pg.

Galli, G. et al., "Automated Machine Learning: A Case Study of Genomic 'Image-Based' Prediction in Maize Hybrids," Front Plant Sci., Mar. 7, 2022, retrieved from the Internet: <https://www.frontiersin.org/articles/10.3389/fpls.2022.845524/full>, 13 pg.

Bazgir, O. et al., "Representation of features as images with neighborhood dependencies for compatibility with convolutional neural networks." Nature communications 11, No. 1 (2020): 1-13.

Bazgir, O. et al. "REFINED (REpresentation of Features as Images with NEighborhood Dependencies): A novel feature representation for Convolutional Neural Networks," arXiv preprint, arXiv:1912.05687, Dec. 11, 2019, 26 pg.

Baltrušaitis, T. et al., "Multimodal machine learning: A survey and taxonomy," IEEE Transactions on Pattern Analysis and Machine Intelligence, Jan. 25, 2018, vol. 41, No. 2, pp. 423-443.

Mell, P. et al., The NIST Definition of Cloud Computing, National Institute of Standards and Technology, U.S. Dept. of Commerce, Special Publication 800-145, Sep. 2011, 7 pg.

* cited by examiner

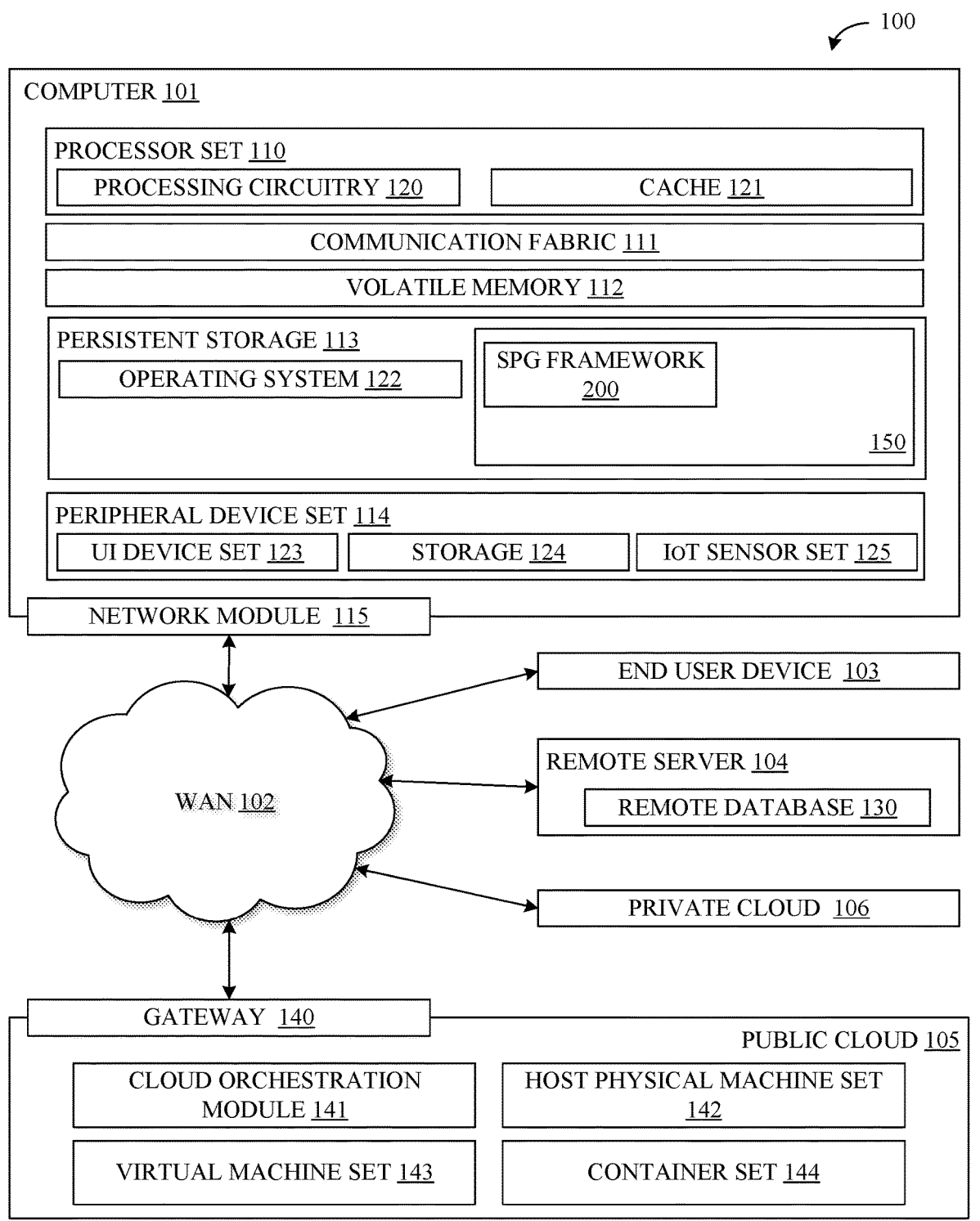

100

COMPUTER 101

PROCESSOR SET 110

PROCESSING CIRCUITRY 120          CACHE 121

COMMUNICATION FABRIC 111

VOLATILE MEMORY 112

PERSISTENT STORAGE 113

OPERATING SYSTEM 122          SPG FRAMEWORK 200

150

PERIPHERAL DEVICE SET 114

UI DEVICE SET 123          STORAGE 124          IoT SENSOR SET 125

NETWORK MODULE 115

WAN 102

END USER DEVICE 103

REMOTE SERVER 104

REMOTE DATABASE 130

PRIVATE CLOUD 106

GATEWAY 140

PUBLIC CLOUD 105

CLOUD ORCHESTRATION MODULE 141          HOST PHYSICAL MACHINE SET 142

VIRTUAL MACHINE SET 143          CONTAINER SET 144

FIG. 1

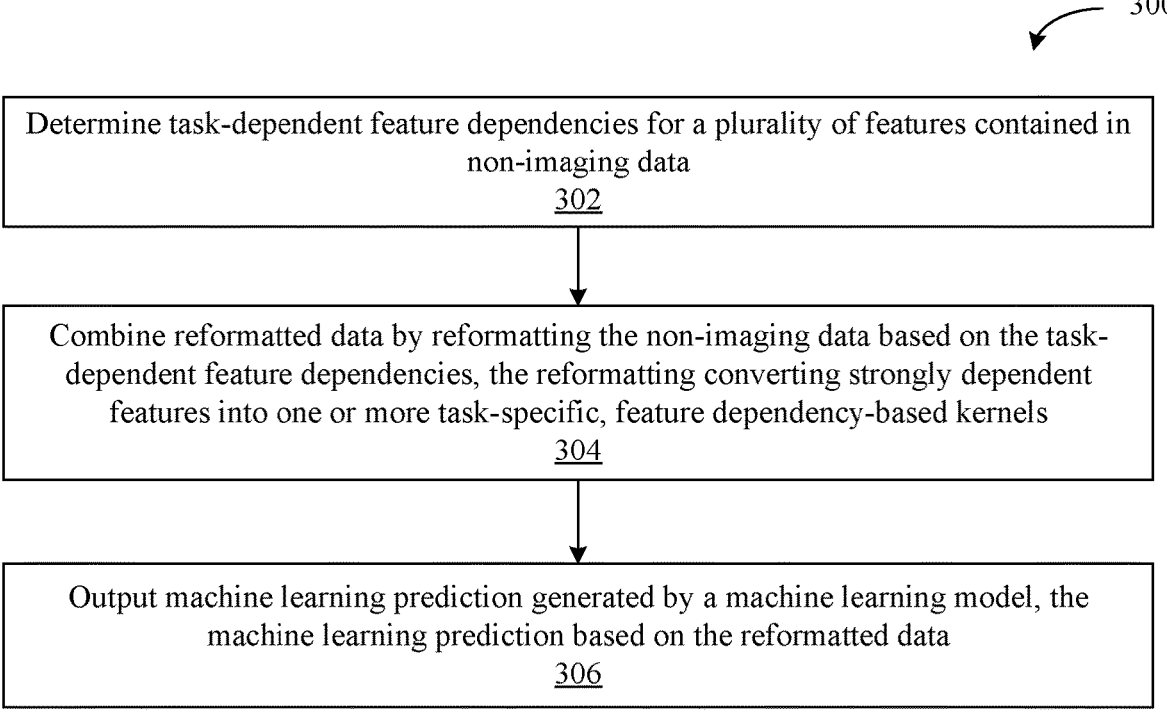

300

Determine task-dependent feature dependencies for a plurality of features contained in non-imaging data
302

Combine reformatted data by reformatting the non-imaging data based on the task-dependent feature dependencies, the reformatting converting strongly dependent features into one or more task-specific, feature dependency-based kernels
304

Output machine learning prediction generated by a machine learning model, the machine learning prediction based on the reformatted data
306

FIG. 3

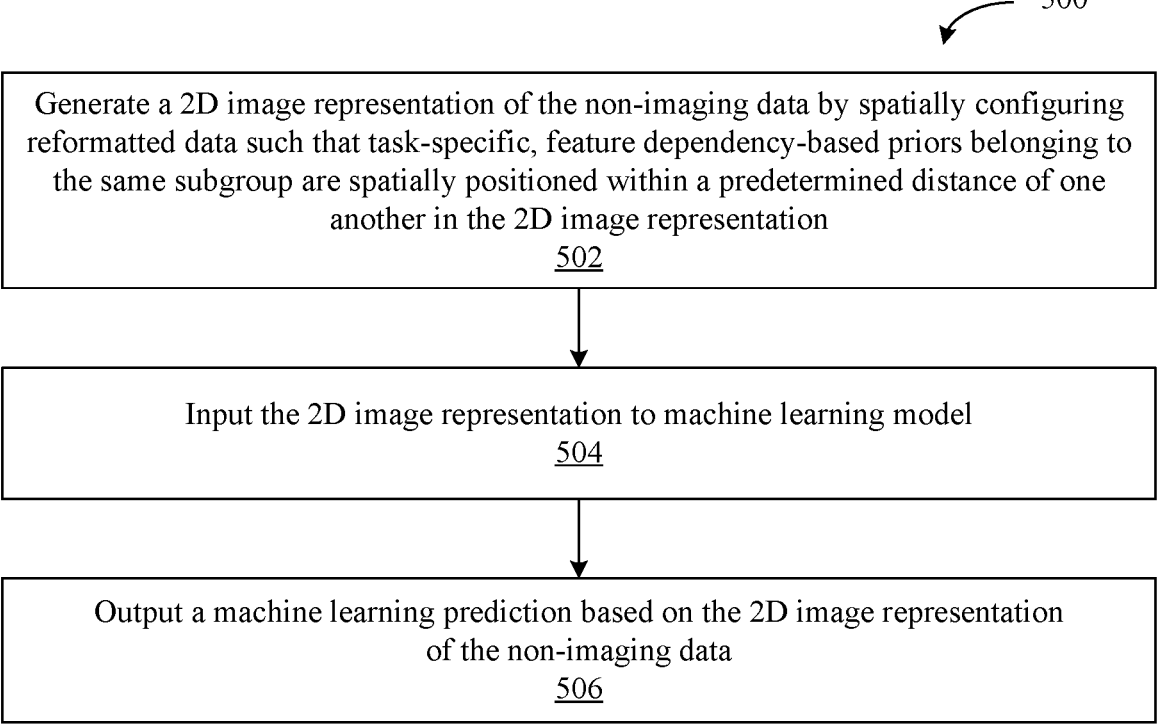

500

Generate a 2D image representation of the non-imaging data by spatially configuring reformatted data such that task-specific, feature dependency-based priors belonging to the same subgroup are spatially positioned within a predetermined distance of one another in the 2D image representation
502

Input the 2D image representation to machine learning model
504

Output a machine learning prediction based on the 2D image representation of the non-imaging data
506

FIG. 5

MACHINE LEARNING FOR NON-IMAGING DATA USING TASK-DEPENDENT FEATURE DEPENDENCIES

BACKGROUND

This disclosure relates to machine learning and, more particularly, to machine learning predictions based on non-imaging data.

Predictions using machine learning or other pattern recognition techniques can be difficult with non-imaging data, at least as compared to imaging data. Imaging data is especially amenable to machine learning techniques, such as convolutional neural networks (CNNs), which can take advantage of the spatial locality of pixels of a two-dimensional (2D) image to discern patterns. Imaging data, moreover, can be formatted to take advantage of spatial priors—that is, features that are spatially structured such that strongly dependent, or highly correlated, features are located closer together. If only those features that are strongly dependent on, or correlated with, one another are located closely together in the input layer of a deep learning neural network (NN), then each node of the NN's first hidden layer need only connect to a small subset of spatial priors. Treating each subset of spatial priors as a kernel can greatly reduce the number of learnable parameters without compromising the NN's predictive accuracy.

Non-imaging data, by contrast, frequently comprises discrete numerical, ordinal, categorical, and/or alphanumeric string data. The nature of non-imaging data does not ordinarily lend itself to formatting based on dependency priors comprising features that are strongly dependent, or highly correlated, with one another. Thus, it can be more difficult to discern patterns in non-imaging data using machine learning techniques such as the CNN because the non-imaging data typically lacks the spatial locality of features such as the pixels of a 2D image.

Nonetheless, the diagnosis and treatment of many diseases, such as lung cancer, tuberculosis, and other health conditions, increasingly depends on non-imaging data as well as radiological or pathological imaging data. Often, effective diagnosis and treatment also depend on multimodal data. Multimodal data includes molecular, genomic, clinical, and other non-imaging data. It is thus likely that future improvements to the understanding of disease mechanisms and in the predicting of treatment outcomes will increasingly depend on combining imaging and non-imaging data. The nature of non-imaging data, however, may not only make predictions using conventional machine learning or other pattern recognition techniques more challenging, but may also constrain opportunities for fusing imaging and non-imaging data for diagnosing and treating various health conditions.

SUMMARY

In one or more embodiments, a method includes determining, with computer hardware, task-dependent feature dependencies for a group of features extracted from non-imaging data received with the computer hardware. The method includes generating, with the computer hardware, reformatted data by reformatting the non-imaging data based on the task-dependent feature dependencies. The reformatting converts strongly dependent features among the group of features into one or more subgroups based on task-specific, feature dependency-based priors. The method includes inputting the reformatted data to a machine learning model implemented in the computer hardware. The method includes outputting, by the computer hardware, a machine learning prediction generated by a machine learning model. The machine learning prediction is based on the reformatted data.

In one aspect, generating the prediction includes generating a 2D image representation of the non-imaging data based on the reformatted data. Within the 2D image representation, task-specific, feature dependency-based priors belonging to a same subgroup are spatially positioned within a predetermined distance of one another. The machine learning prediction is based on the reformatted data as presented in the 2D image representation.

In another aspect, the task-dependent feature dependencies are determined based on pairwise correlations among the group of features. The pairwise correlations, in one aspect, are conditional correlations conditioned one of a plurality of classes associated with the non-imaging data.

In another aspect, the machine learning prediction is performed using a convolutional neural network.

In another aspect, the non-imaging data is fused with imaging data selected based on a predetermined commonality with the non-imaging data. The imaging data, in one aspect, is radiological imaging data or pathological imaging data, and the non-imaging data is molecular data, genomic data, clinical data, and/or demographic data.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

FIG. 1 illustrates an example of a computing environment that is capable of implementing an executable framework for task-dependent, feature dependency-based machine learning.

FIG. 3 illustrates an example method of operation of the framework of FIGS. 1 and 2.

FIG. 5 illustrates an example method of operation of an optional feature of the framework of FIGS. 1 and 2.

DETAILED DESCRIPTION

Figure 2:
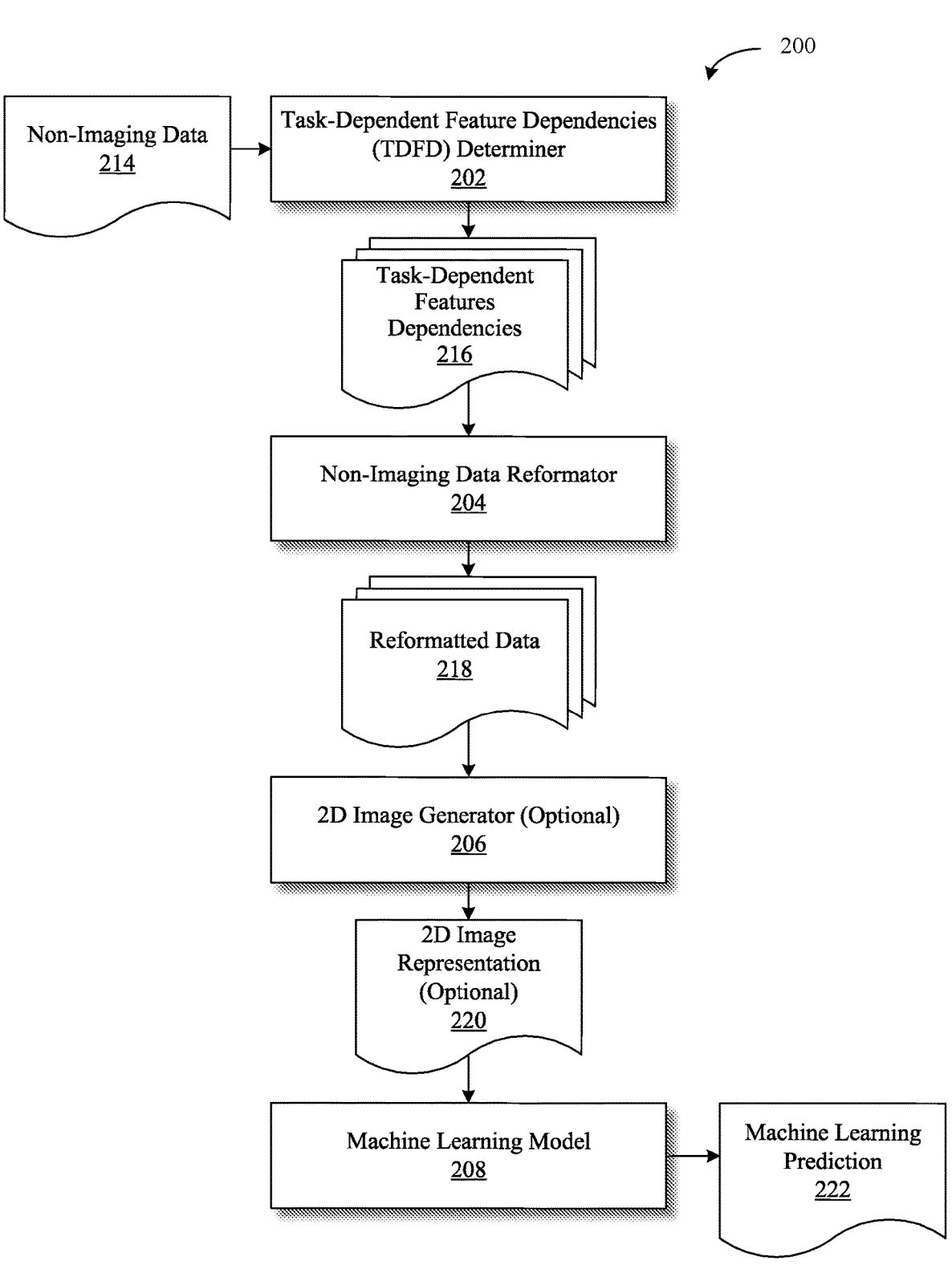
FIG. 2 illustrates an example architecture for the executable framework illustrated in FIG. 1.

While the disclosure concludes with claims defining novel features, it is believed that the various features described within this disclosure will be better understood from a consideration of the description in conjunction with the drawings. The process(es), machine(s), manufacture(s) and any variations thereof described herein are provided for purposes of illustration. Specific structural and functional details described within this disclosure are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to machine learning and, more particularly, to machine learning predictions based on non-imaging data. In accordance with the inventive arrangements described herein, methods, systems, and computer program products are provided that are capable of determining task-dependent feature dependencies among features of non-imaging data. The determination of task-specific dependencies can be used to create task-specific, feature dependency-based priors, which can facilitate machine learning by making the training of a machine learning model more efficient and by enhancing the predictive accuracy of the machine learning model.

As defined herein, "feature dependency" means a strong correlation or other predetermined association between data features. In certain arrangements, the strength of a feature dependency can be quantitatively measured by a statistic such as a correlation coefficient (e.g., Pearson correlation coefficient). "Task-dependent feature dependency," as defined herein, means a strong dependency or correlation (positive or negative) between features whose dependency stems from a shared machine learning task (e.g., classification). The task dependency thus excludes features whose dependency is due only to confounding factors that do not relate to the same machine learning task. The strength of a task-dependent feature dependency, in certain arrangements, can be quantitatively measured by a conditional correlation, the condition based on the specific machine learning task. As defined herein, "task-specific, feature dependency-based priors" are features having a strong dependency stemming from a shared machine learning task, where prior refers to prior knowledge regarding how the features are related to one another. The purpose of grouping strongly dependent features based on priors is to form meaningful joint patterns that can be discovered through machine learning.

In one aspect, task-dependent feature dependency can be used to create spatial priors in constructing a 2D image representation of non-imaging data. "Spatial priors," as defined herein, are task-specific, feature dependency-based priors features having a strong dependency stemming from a shared machine learning task and that are spatially located close together within an image representation. Thus, an aspect of a 2D image representation having spatial priors created using task-dependent, feature dependency is that the spatial priors provide a spatial structure such that strongly dependent features (the spatial priors) are located in close proximity to one another (e.g., in a single neighborhood) within a 2D image.

In the context of deep learning NNs, features identified as spatial priors based on the strength of dependency allows the features to be located together in the input layer. Each node in the first hidden layer need only connect to a small subset of strongly dependent features—that is, a group of spatial priors. This results in considerable reduction in the number of learnable parameters without comprising the training or predictive accuracy of the underlying machine learning model. In one aspect of the inventive arrangements, a CNN efficiently implements a spatial priors-based model simplification by sharing convolutional priors among all nodes in the hidden layer, making detection of local feature patterns location invariant.

Another aspect of the inventive arrangements disclosed herein is various mechanisms for constructing a 2D image representation of non-imaging data. The 2D image representation is constructed with spatial priors created based on task dependent feature dependency. The 2D image representation with spatial priors enables the analysis of non-imaging data using machine learning techniques such as the CNN which are especially well-suited for analyzing imaging data. Spatial priors are often lacking in non-imaging data. For example, most clinical features are not spatially structured. Genomic data may be spatially structured, but usually does not satisfy the distance-related feature dependency requirement. Some conventional approaches apply dimension reduction to project features onto a 2D plane, but a limitation of these approaches is that multiple features may be projected to the same pixel in the resulting image representation and may require multidimensional scaling. The inventive arrangements disclosed herein provide efficient and effective mechanisms for creating spatial priors that overcome these limitations.

Still another aspect of the inventive arrangements is creating task-specific, feature dependency-based priors in a way that does not rely on generic feature dependency. Generic feature dependency may be caused by confounding factors. Confounding pertains to causality and is not addressed by correlation. A confounding factor is one that affects both an independent variable and a dependent variable, which can give rise to a spurious association between the variables. If, for some data, two data features' dependency is due to confounding factors unrelated to the machine learning task (e.g., classification), then a joint pattern of the features may not be helpful, and indeed, may be problematic. The inventive arrangements overcome the problems stemming from a possible presence of confounding factors. The inventive arrangements overcome the problems by conditioning feature dependency on a machine learning task that is shared by dependency priors. Specifically, the inventive arrangements provide a mechanism for creating task-specific, feature dependency-based priors that are conditioned on a shared machine learning task. The task-based conditioning of feature dependency eliminates the problem of confounding among feature dependency-based priors.

Further aspects of the inventive arrangements are described below with reference to the figures. For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Referring to FIG. 1, computing environment 100 contains an example of an environment for the execution of at least some of the computer code in block 150 involved in performing the inventive methods, such as task-dependent, feature dependency-based machine learning (TDFD/ML) framework 200 implemented as executable program code or instructions. TDFD/ML framework 200 is capable of determining task-dependent feature dependencies for a plurality of features contained in non-imaging data. The non-imaging data can be reformatted based on the task-dependent feature dependencies. A machine learning prediction (e.g., classification or regression) can be generated based on the reformatted data. Optionally, TDFD/ML framework 200 can be implemented to create spatial priors from the non-imaging data based on the task-dependent feature dependencies. Using the spatial priors, a 2D spatial representation of the non-imaging data can be generated. The 2D spatial representation can enable predictions based on the non-imaging data using a machine learning model more suited for processing imaging data, such as a CNN.

Computing environment 100 additionally includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and ABC/ML TDFD/ML framework 200, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

Computer 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

Processor set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 150 in persistent storage 113.

Communication fabric 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

Persistent storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid-state storage devices. Operating system 122 may take several forms, such as various known proprietary operating systems or open-source Portable Operating System Interface type operating systems that employ a prior. The code included in block 150 typically includes at least some of the computer code involved in performing the inventive methods.

Peripheral device set 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (e.g., secure digital (SD) card), connections made though local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (e.g., where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

Network module 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (e.g., embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (e.g., the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

End user device (EUD) 103 is any computer system that is used and controlled by an end user (e.g., a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

Remote server 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the prior allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (e.g., private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

FIG. 2 illustrates an example architecture for the executable TDFD/ML, framework 200 of FIG. 1. Illustratively, TDFD/ML, framework 200 includes task-dependent feature dependencies (TDFD) determiner 202, non-imaging data (NID) reformator 204, and machine learning model 208. Optionally, in some embodiments, TDFD/ML, framework 200 also includes 2D image generator 206.

FIG. 3 illustrates an example method 300 of operation of TDFD/ML, framework 200 illustrated in FIGS. 1 and 2.

Referring jointly to FIGS. 2 and 3, TDFD determiner 202, in block 302, determines task-dependent feature dependencies 216 for features extracted from non-imaging data 214.

Non-imaging data 214 can be structured as a set of samples $$X = \{\bar{x}_i\}_{i=1}^N,$$

where the data structure of each sample is a feature vector $$\bar{x}_i = \{x_i^{(1)}, \dots, x_i^{(N)}\}.$$

For training machine learning model 208, the set $$X = \{\bar{x}_i\}_{i=1}^N$$

can comprise labeled training samples. A label $y_i$ is assigned to each $\bar{x}_i \in X$. $y_i \in \{0,1\}$ for training machine learning model 208 as a binary classifier, and $y_i \in \{1, \dots, L\}$ for training machine learning model 208 as a multi-class classifier (with respect to classes 1 through L).

In block 302, TDFD determiner 202 can determine dependencies based on pairwise dependency scores for the features extracted from non-imaging data 214. A dependency score $$r_C(x_i^j, x_i^k)$$

generated by TDFD determiner 202 measures the degree to which the j-th feature (treated as a random variable) of the i-th sample is related to the k-th feature (also treated as a random variable) of the i-th sample. One such measure is statistical covariance, which can be normalized to generate a correlation coefficient. The correlation coefficient measures how good a prediction of the value of one of random variable (feature) is when the prediction is based on the value of another random variable (feature). TDFD determiner 202, in certain embodiments, determines dependency scores based on the Pearson correlation:

$$r_C(j, k) = \frac{\sum_{i=1}^N (x_i^j - E[x^j])(x_i^k - E[x^k])}{\sqrt{\sum_{i=1}^N (x_i^j - E[x^j])^2} \sqrt{\sum_{i=1}^N (x_i^k - E[x^k])^2}}$$

Non-imaging data 214 may include a set C of confounding features c. As noted above, confounding features relate to causality that is not captured through correlation. Creating dependency priors based on features whose dependency stems from confounding factors does not enhance machine learning. Accordingly, the feature dependencies determined by TDFD determiner 202 are task specific. Task-dependent feature dependencies 216 can be determined by TDFD determiner 202 based on a task-specific feature dependency score $r_{c_y}(j, k)$ in accordance with the following approach:

$$r_{c_y}(j, k) \sim r_C(j, k) - r_{C \setminus c_y}(j, k),$$

where $c_y$ denotes the set of features corresponding to a specific task (e.g., identifying a pattern associated with label y) and where $r_{C \setminus c_y}$ is a dependency score due to all confounding features other than the $c_y$. Applying the Pearson correlation (above) as a conditional correlation, in which the correlation is conditioned on a sample's class, y=1, $r_{C \setminus c_y}$ is:

$$r_{C \setminus c_y}(j, k) = \sum_{l=0}^1 r_C(j, k | y = l) p(y = l)$$

where p(y=1) is the probability that the sample's class is 1 (e.g., zero or one for a binary classifier), such that $$r_C(j, k | y = l) =$$

$$\frac{\sum_{i \in (y_i = l)} (x_i^j - E[x^j | y = l])(x_i^k - E[x^k | y = l])}{\sqrt{\sum_{i \in (y_i = l)} (x_i^j - E[x^j | y = l])^2} \sqrt{\sum_{i \in (y_i = l)} (x_i^k - E[x^k | y = l])^2}}$$

Dependencies among features can vary inversely as well as directly. Accordingly, $r_{c_y}$ can take on negative as well as positive values. Taking into account both positive and negative values for $r_{c_y}$ an overall pairwise measure of task-dependent feature dependencies 216 can be determined as $$R(j, k) = |r_{c_y}(j, k)|$$

The determination of task-dependent feature dependencies 216 using the procedures performed by TDFD determiner 202 applies with respect to multi-category classifica-
tions l={1, . . . , L} as well as binary classifications.
Accordingly, with respect to multi-category classifications,
TDFD determiner 202 can compute the overall pairwise
feature dependency for task-dependent feature dependencies
216 as $$R(j, k) = \sum_{l=1}^{L} \left| r_{c_y}(j, k) \right|$$

High values for the dependency scores $$\left| r_{c_y}\left(x_i^j, x_i^k\right) \right|$$

correspond to strong task-dependent feature dependencies.
Strong dependencies are likely to have distinctive patterns
for performing the specific tasks (e.g., classification, regres-
sion) of a machine learning model 208. Thus, identifying
task-dependent feature dependencies 216 can enhance the
predictive accuracy of machine learning model 208,
described below. Identifying task-dependent feature depen-
dencies 216 facilitates the efficient training of machine
learning model 208.

In block 304, non-imaging data reformator 204 generates
reformatted data 218 by reformatting non-imaging data 214
based on task-dependent feature dependencies 216. The
reformatting of non-imaging data 214 by reformator 204
converts strongly dependent features determined by TDFD
determiner 202 into one or more task-specific, feature
dependency-based priors.

Figure 4A:
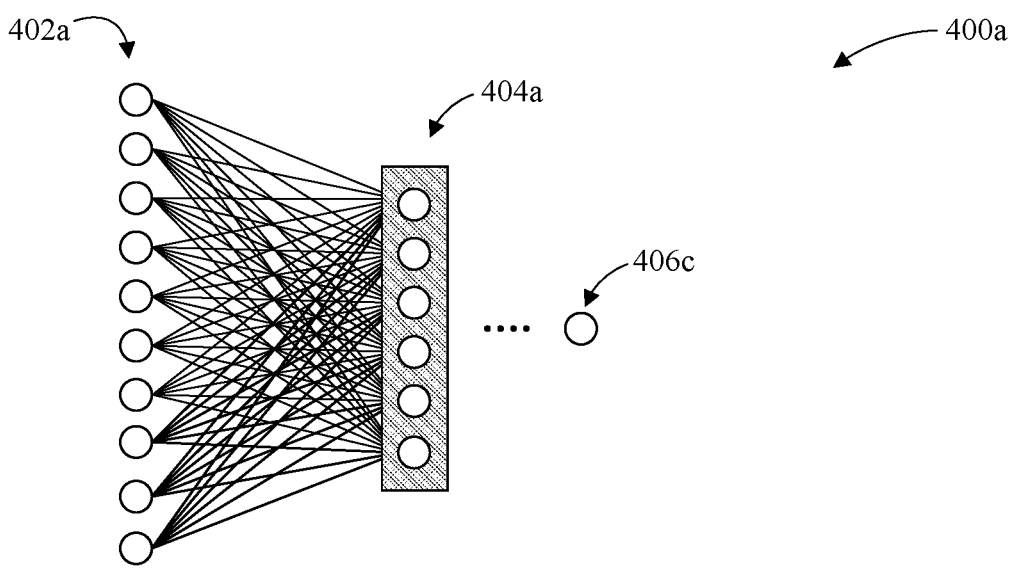
FIGS. 4A and 4B illustrate certain aspects of implementing machine learning using the framework of FIGS. 1 and 2.
Figure 4B:
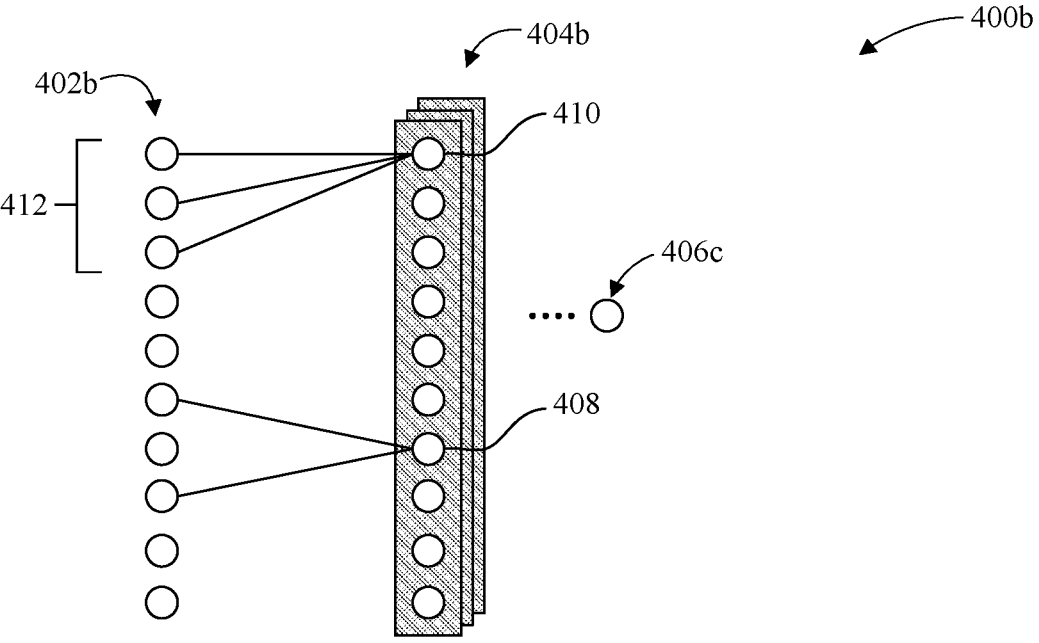

Referring additionally to FIGS. 4A and 4B, an advantage
of the reformatting of non-imaging data 214 based on
task-dependent feature dependencies 216 is illustrated.
FIGS. 4A and 4B illustrate, respectively, NN 400a and NN
400b. NN 400a illustratively includes input layer 402a, first
hidden layer 404a, and output layer 406a. NN 400b illus-
tratively includes input layer 402b, first hidden layer 404b,
and output layer 406c. NN 400a and NN 400b are each a
different implementation of machine learning model 208.
NN 400a is fully connected. Without any knowledge of
feature dependencies, the n nodes (features) of input layer
402a need to connect to each of k nodes of first hidden layer
404a to detect potential patterns in input data. The number
of nodes of first hidden layer 404a is related to the number
of patterns to be detected by NN 400a. Thus, NN 400a is a
fully connected network. The number of learnable param-
eters in first hidden layer 404a is O(nk).

Reformatting non-imaging data 214 based on task-depen-
dent feature dependencies 216 allows machine learning
model 208 to be restructured such that input layer 402b of
NN 400b need only sparsely connect to first hidden layer
404b Grouping strongly dependent features into one or more
subgroups based on task-specific, feature dependency-based
priors for input to the input layer 402b, allows first hidden
layer 404b to be configured as kernels. Each kernel connects
to only one subgroup of features based on task-specific,
feature dependency-based priors. For example, the two
nodes of input layer 402b that connect to node 408 of first
hidden layer 404b is illustratively a subgroup. The three
nodes that connect to node 410 of first hidden layer 404b are
spatially located close to one another and can form neigh-
borhood 412. As described below with reference to spatial
priors, a neighborhood such as 412, which contains the input layer 402b nodes connected to node 410 of first hidden layer
404b, facilitates the generation of a 2D image representation
of non-imaging data 214. Note that various sparse connec-
tions of the other nodes in input layer 402b with the nodes
of first hidden layer 404b are implicit and are not shown
explicitly in the figure. NN 400b is solely for purpose of
illustration. Other network constructions (e.g., graph neural
network) are implemented in other embodiments.

With machine learning model 208 implemented as NN
400b, rather than all n nodes (features) of input layer 402b
connecting to the k nodes of first hidden layer 404b, only
c<n subgroups of task-specific, feature dependency-based
priors do so. The number of learnable parameters in first
hidden layer 404b is therefore only O(ck). The reduction in
the number of learnable parameters can be considerable,
especially if the number of features, n, is large. A consid-
erable reduction of learnable parameters is achieved, but
without compromising the effectiveness of the underlying
machine learning. The reduction enhances the efficiency
with which machine learning model 208 is trained, as well
as the predictive accuracy of the model once trained. Model
simplification also lessens the load on computer hardware
resources needed for training and using the model, thus also
enhancing the efficiency of the underlying computer hard-
ware.

Referring still to FIGS. 2 and 3, in block 306, non-
imaging data reformator 204 inputs reformatted data 218 to
machine learning model 208. In block 308, machine learning
model 208 outputs machine learning prediction 222.
Machine learning prediction 222 is generated by machine
learning model 208 based on the reformatted data 218.

Referring now to FIGS. 2 and 5 collectively, TDFD/ML,
framework 200 in some embodiments includes 2D image
generator 206. 2D image generator 206 is capable of gen-
erating 2D image representation 220, a 2D image represent-
ing non-imaging data 214. Representing non-imaging data
as a 2D image allows the non-imaging data to be analyzed
using machine learning techniques, such as a CNN, which
are especially efficient for processing and analyzing spatially
structured data. FIG. 5 illustrates an example method 500 of
operation of 2D image generator 206.

In block 502, 2D image generator 206 generates two-
dimensional 2D image representation 220 of the non-imag-
ing data 214 by configuring reformatted data 218. 2D image
generator 206 spatially configures reformatted data 218 such
that task-specific, feature dependency-based priors that
belong to the same subgroup are positioned as spatial priors
within a predetermined distance of one another in 2D image
representation 220.

In certain embodiments, 2D image generator 206 groups
and positions spatial priors within a predetermined distance
of one another by iteratively searching for an optimal spatial
configuration $\pi^*$ over a set of feasible alternative configu-
rations $\pi$. For each configuration $\pi$, 2D image generator 206
quantifies the strength of dependency, $D(\pi)$, among neigh-
boring features based on the above-defined overall pairwise
feature dependency $R(j, k)$:

$$D(\pi) = \sum_{j=1}^{n} \sum_{k \in N_\pi(j)} e^{-d_\pi(j,k)/\sigma} R(j, k)$$

where $\mathcal{N}_\pi(j)$ is a neighborhood for feature j based on spatial
configuration $\pi$ of the spatial priors and $d_\pi(j, k)$ is a distance (e.g., Euclidean distance) between the location of feature j and the location of feature k in the configuration π of a feasible 2D image.

To maximize feature dependencies for neighboring features, an optimal spatial configuration $$\pi^* = \mathrm{argmax}_\pi D(\pi)$$

can be determined by 2D image generator 206's implementing a greedy algorithm that searches over the feasible configurations π for a local optimal solution π*. Initially, the feature with the maximal pairwise dependency score $$\mathrm{argmax}_j \sum_k |R(j, k)|$$

with respect to the remaining features is identified and placed in the middle of the configuration π of a feasible 2D image. Remaining unplaced features are iteratively placed one at a time in the configuration π of the feasible 2D image on 2D image representation 220 by expanding the region containing the placed features. The feature placed at iteration i maximizes the following difference $$D(\pi^i) - D(\pi^{i-1})$$

where $\pi^i$ contains the feature configuration π of the feasible 2D image produced at the i-th iteration and D(π*) is an overall feature dependency score for the positioning of the features.

Upon conclusion of the iterative process, 2D image generator 206 generates 2D image representation 220 whereby the spatial priors are positioned in accordance with the determination of the local optima π*.

At block 504, 2D image representation 220 is input to machine learning model 208. At block 506, machine learning model 208 outputs machine learning prediction 222, machine learning prediction 222 based on 2D image representation 220's representation of non-imaging data 214.

Leveraging spatial priors created based on task-dependent feature dependencies, enables construction of a 2D image representation on non-imaging data. This, in turn, enables the non-imaging data to be processed and analyzed using machine learning techniques such as CNNs that are especially well-suited for use with imaging data. Using a CNN for the non-imaging data represented as 2D image, for example, allows the CNN to share dependency priors (e.g., convolutional priors) among all nodes in a hidden layer, making local feature pattern detection location invariant.

In other applications, reformatting non-imaging data based on task-dependent feature dependencies enables the fusing, or joining, of non-imaging and imaging data based on a predetermined commonality. "Fusing," as defined herein, means combining non-imaging data and imaging data into a single data set. This can be beneficial, for example, with respect to healthcare-related machine learning where the commonality may be diagnosing, treating, and/or studying health conditions. The commonality can be, for example, a patient or an epidemiological study. With a fusing of non-imaging and imaging data, for example, radiological imaging data and/or pathological imaging data can be fused with multimodal data, such as molecular data, genomic data, clinical data, and/or demographic data. In the case of diagnosis and treatment of a disease, for example, patient-specific imaging data (e.g., pathological, radiological), suited for input to a CNN, can be fused with a 2D image representation of non-imaging data (e.g., clinical, demographic) relating to the patient.

The terminology used herein is for the purpose of describing particular embodiments only and is not intended to be limiting. Notwithstanding, several definitions that apply throughout this document now will be presented.

The term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "one embodiment," "an embodiment," "in one or more embodiments," "in particular embodiments," or similar language mean that a particular feature, structure, or characteristic described in connection with the embodiment is included in at least one embodiment described within this disclosure. Thus, appearances of the aforementioned phrases and/or similar language throughout this disclosure may, but do not necessarily, all refer to the same embodiment.

As defined herein, the term "output" means storing in physical memory elements, e.g., devices, writing to display or other peripheral output device, sending or transmitting to another system, exporting, or the like.

As defined herein, the term "processor" means at least one hardware circuit configured to carry out instructions. The instructions may be contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "responsive to" means responding or reacting readily to an action or event. Thus, if a second action is performed "responsive to" a first action, there is a causal relationship between an occurrence of the first action and an occurrence of the second action. The term "responsive to" indicates the causal relationship.

The term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms first, second, etc. may be used herein to describe various elements. These elements should not be limited by these terms, as these terms are only used to distinguish one element from another unless stated otherwise or the context clearly indicates otherwise.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:

determining, with computer hardware, task-dependent feature dependencies for a group of features extracted from non-imaging data received with the computer hardware;

generating, with the computer hardware, reformatted data by reformatting the non-imaging data based on the task-dependent feature dependencies, wherein the reformatting converts strongly dependent features among the group of features into one or more subgroups based on task-specific, feature dependency-based priors;

generating, by an image generator, a two-dimensional (2D) image representation of the non-imaging data by configuring the reformatted data into the 2D image representation;

inputting the 2D image representation to a machine learning model implemented with the computer hardware, wherein the machine learning model is trained using the strongly dependent features, of the group of features, that exclude features unrelated to a machine learning task;

generating, using the machine learning model, a machine learning prediction based on the reformatted data as configured in the 2D image representation; and outputting, by the computer hardware, the machine learning prediction.

2. The computer-implemented method of claim 1, further comprising:

configuring the reformatted data into the 2D image representation, wherein the configuring of the reformatted data comprises positioning the task-specific, feature dependency-based priors belonging to a same subgroup of the one or more subgroups as spatial priors in the 2D image representation, and each spatial prior of the spatial priors is positioned within a predetermined distance from remaining spatial priors of the spatial priors.

3. The computer-implemented method of claim 1, wherein the task-dependent feature dependencies are determined based on pairwise correlations among the group of features.

4. The computer-implemented method of claim 3, wherein the pairwise correlations are conditional correlations, and the pairwise correlations are conditioned to one class of a plurality of classes associated with the non-imaging data.

5. The computer-implemented method of claim 1, wherein the machine learning prediction is performed using a convolutional neural network.

6. The computer-implemented method of claim 1, further comprising:

fusing the non-imaging data with imaging data, wherein the imaging data is selected based on a predetermined commonality with the non-imaging data.

7. The computer-implemented method of claim 6, wherein the imaging data is selected from the group consisting of radiological imaging data and pathological imaging data, and the non-imaging data selected from the group consisting of molecular data, genomic data, clinical data, and demographic data.

8. A system, comprising:

a processor configured to execute operations comprising:

determining task-dependent feature dependencies for a group of features extracted from non-imaging data received with computer hardware;

generating reformatted data by reformatting the non-imaging data based on the task-dependent feature dependencies, wherein the reformatting converts strongly dependent features among the group of features into one or more subgroups based on task-specific, feature dependency-based priors;

generating, by an image generator, a two-dimensional (2D) image representation of the non-imaging data by configuring the reformatted data into the 2D image representation;

inputting the 2D image representation to a machine learning model implemented with the computer hardware, wherein the machine learning model is trained using the strongly dependent features, of the group of features, that exclude features unrelated to a machine learning task;

generating, using the machine learning model, a machine learning prediction based on the reformatted data as configured in the 2D image representation; and outputting, by the computer hardware, the machine learning prediction.

9. The system of claim 8, wherein the processor is further configured to execute the operations including configuring the reformatted data into the 2D image representation, wherein the configuring of the reformatted data comprises positioning the task-specific, feature dependency-based priors belonging to a same subgroup of the one or more subgroups as spatial priors in the 2D image representation, and each spatial prior of the spatial priors is positioned within a predetermined distance from remaining spatial priors of the spatial priors.

10. The system of claim 8, wherein the task-dependent feature dependencies are determined based on pairwise correlations among the group of features.

11. The system of claim 10, wherein the pairwise correlations are conditional correlations, and the pairwise correlations are conditioned to one class of a plurality of classes associated with the non-imaging data.

12. The system of claim 8, wherein the machine learning prediction is performed using a convolutional neural network.

13. The system of claim 8, wherein the processor is further configured to execute the operations including fusing the non-imaging data with imaging data, wherein the imaging data is selected based on a predetermined commonality with the non-imaging data.

14. A computer program product, comprising:

one or more computer-readable storage media and program instructions collectively stored on the one or more computer-readable storage media, the program instructions executable by a processor to cause the processor to execute operations comprising:

determining task-dependent feature dependencies for a group of features extracted from non-imaging data received with computer hardware;

generating reformatted data by reformatting the non-imaging data based on the task-dependent feature dependencies, wherein the reformatting converts strongly dependent features among the group of features into one or more subgroups based on task-specific, feature dependency-based priors;

generating, by an image generator, a two-dimensional (2D) image representation of the non-imaging data by configuring the reformatted data into the 2D image representation;

inputting the 2D image representation to a machine learning model implemented with the computer hardware, wherein the machine learning model is trained using the strongly dependent features, of the group of features, that exclude features unrelated to a machine learning task;

generating, using the machine learning model, a machine learning prediction based on the reformatted data as configured in the 2D image representation; and outputting, by the computer hardware, the machine learning prediction.

15. The computer program product of claim 14, wherein the program instructions further cause the processor to execute the operations including configuring the reformatted data into the 2D image representation, wherein the configuring of the reformatted data comprises positioning the task-specific, feature dependency-based priors belonging to a same subgroup of the one or more subgroups as spatial priors in the 2D image representation, and each spatial prior of the spatial priors is positioned within a predetermined distance from remaining spatial priors of the spatial priors.

16. The computer program product of claim 14, wherein the task-dependent feature dependencies are determined based on pairwise correlations among the group of features.

17. The computer program product of claim 16, wherein the pairwise correlations are conditional correlations, and the pairwise correlations are conditioned to one class of a plurality of classes associated with the non-imaging data.

18. The computer program product of claim 14, wherein the machine learning prediction is performed using a convolutional neural network.

19. The computer program product of claim 14, wherein the program instructions further cause the processor to execute the operations including fusing the non-imaging data with imaging data, wherein the imaging data is selected based on a predetermined commonality with the non-imaging data.

20. The computer program product of claim 19, wherein the imaging data is selected from the group consisting of radiological imaging data and pathological imaging data, and the non-imaging data selected from the group consisting of molecular data, genomic data, clinical data, and demographic data.

* * * * *